United States Patent [19]

Oliva

[11] 4,189,838
[45] Feb. 26, 1980

[54] METHOD FOR REMOVING RESTORATIONS FROM TEETH

[76] Inventor: Richard A. Oliva, 3318 Club Dr., Los Angeles, Calif. 90064

[21] Appl. No.: 2,441

[22] Filed: Jan. 10, 1979

Related U.S. Application Data

[63] Continuation of Ser. No. 958,051, Nov. 6, 1978, abandoned, which is a continuation of Ser. No. 820,426, Aug. 1, 1977, abandoned.

[51] Int. Cl.² .................................................. A61C 3/16
[52] U.S. Cl. ....................................... 433/167; 433/25
[58] Field of Search ..................... 32/43, 44, 45, 40 R, 32/61, 62

[56] References Cited
U.S. PATENT DOCUMENTS

| | | | |
|---|---|---|---|
| 2,937,446 | 5/1960 | Weisenfeld | 32/40 R |
| 3,903,606 | 9/1975 | Oliver | 32/40 R |

*Primary Examiner*—Louis G. Mancene
*Assistant Examiner*—John J. Wilson
*Attorney, Agent, or Firm*—Keith D. Beecher

[57] ABSTRACT

A method and means for removing firmly affixed, binding, stuck or cemented dental restorations and appliances, which includes a substance which when held under compressive force forms strong adhesive properties between opposing surfaces sufficient to remove firmly affixed, binding, stuck or cemented dental restorations and appliances. The substance forms a strong temporary adhesive bond due to its strong adhesive properties developed under compression between the surface of the restoration or appliance to be removed and the instrumentality performing the removal, this being achieved with no tools or mechanical devices. The instrumentality, for example, comprises the jaws of the patient which are used to apply compressing force and a forceful rapid jerking reverse removal pressure to the restoration or appliance by the muscular force of the patient's jaw opening.

9 Claims, 21 Drawing Figures

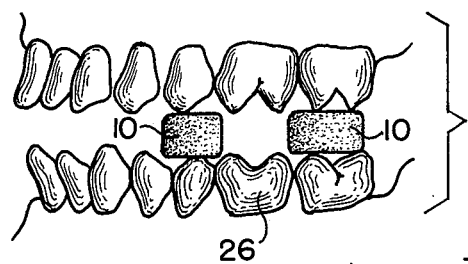
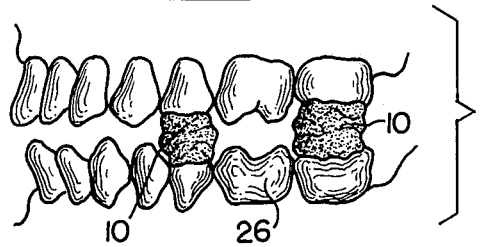
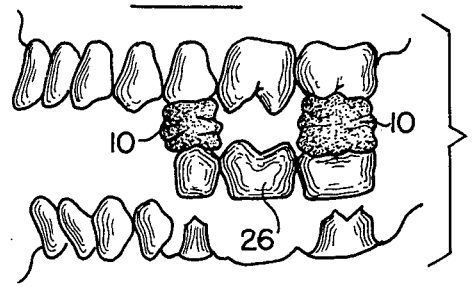
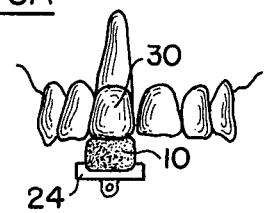
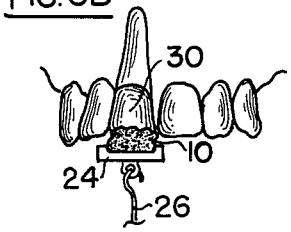
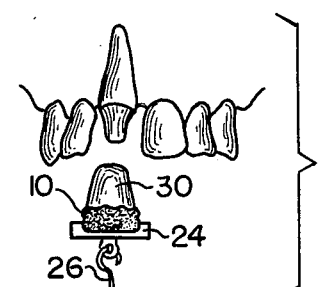
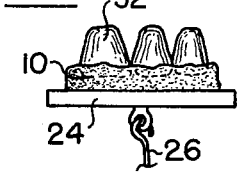
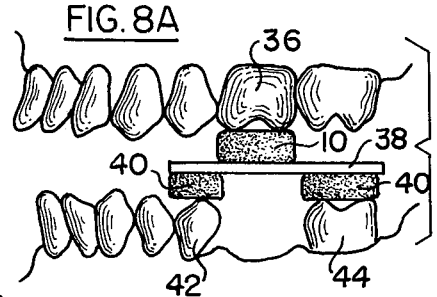
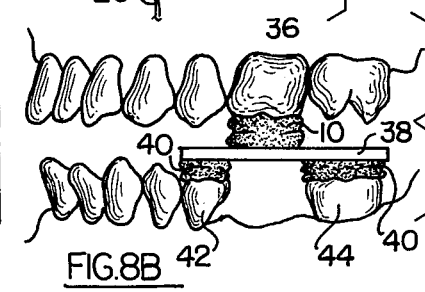
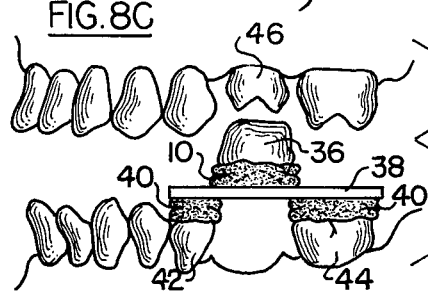
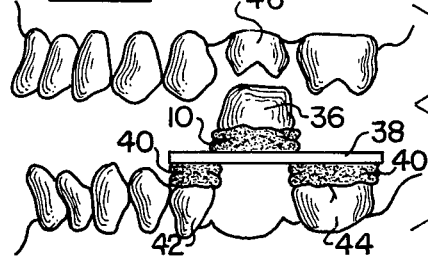
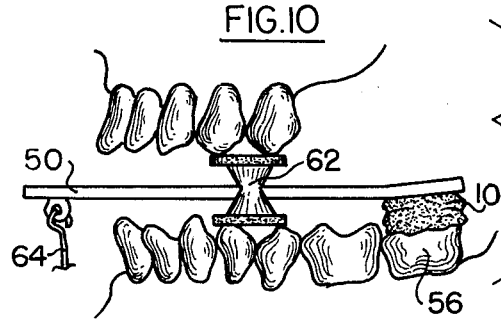
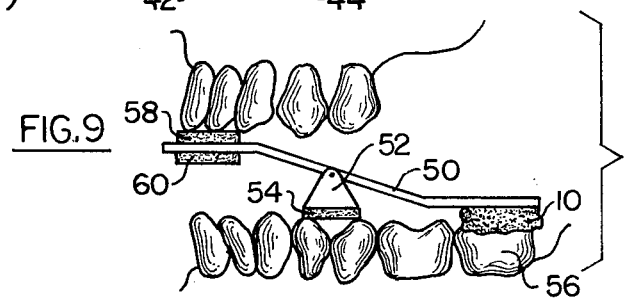

METHOD FOR REMOVING RESTORATIONS FROM TEETH

This application is a continuation of copending application Ser. No. 958,051 filed for Richard A. Oliva on Nov. 6, 1978, and now abandoned, which in turn, is a continuation of application Ser. No. 820,426 filed for Richard A. Oliva on Aug. 1, 1977, now abandoned, and entitled "METHOD AND MEANS FOR REMOVING RESTORATIONS FROM TEETH."

BACKGROUND OF THE INVENTION

Dental restorations are single or multiple units, such as crowns, jackets, inlays, bridges, formed of many types of materials, and used in dentistry to restore teeth. These materials may include, for example, gold; gold and porcelain; semi-precious and other metals by themselves, or combined with porcelain; resin or plastic.

Dental restorations are firmly bonded to natural teeth or their roots by a cementing medium. It is well known that the removal of a cemented dental restoration may be necessary upon the occurrence of dental decay, or in order to examine the vitality and pulpal involvement of a prepared tooth, or for other reasons. In the prior art, the removal of firmly affixed, binding, stuck or cemented dental restorations, such as bridges or crowns, was achieved by the application of a mechanical grasping means to the restoration followed by the application of a direct or leverage force in a direction to break the cement bond. In the prior art, for example, dental restorations have been removed by means of clamps, reverse mallets, hammer and chisels, or by drilling a hole and using a screw post in the resortation, and combination of claws, jaws and screws, all of which serve to distort the restoration by bending its margins, or by destroying the integrity of the restoration by a hole, or by torquing action which often results in tooth fracture.

The present invention provides an improved method for removing all types of firmly affixed, binding, stuck or cemented dental restorations and dental appliances, utilizing a malleable substance composed of any combination of materials, natural or artificial, which together create a substance with such adhesive qualities when compressed under pressure between two surfaces as to form a strong temporary bond between the surface of the restoration or appliance being removed and the opposing tooth or teeth when compressed between the surfaces with at least 25 pounds pressure compressing the substance to 50–75% of its bulk.

The substance when placed in contact and compressed on the surface of the restoration or appliance with sufficient force forms a temporary adhesive level sufficient to remove the restoration or appliance, firmly affixed, binding, stuck or cemented, from the tooth or teeth, when a forceful reverse pressure is applied by the muscular force of the patient in opening their jaws in a rapid, forceful jerking movement, or by a combination of muscular force of the patient and added external forces, or by external forces only, all directed in a direction parallel with the long axis of the tooth, and in the reverse direction to that which the restoration or appliance was initially placed on or in the tooth. The technique of using such a substance allows for convenient single or multiple firmly affixed, binding, stuck or cemented restoration or appliance removal for any reason deemed necessary.

The method and means of the invention has an advantage over all other methods and means presently available for the removal of firmly affixed, binding, stuck or cemented dental restorations and appliances in that:

1. A strong temporary adhesive bond with the surface of the restoration or appliance to be removed is used, and there is no requirement for drilling a hole, cutting a groove or notch, or mechanically clamping to the sides or margins of the restorations, or using any tool as is the case in the prior art, all of which in one way or another either deform, distort or destroy the integrity of the restoration and which can create severe tooth, periodontal and patient trauma.

2. The substance forming the strong temporary adhesive bond can be easily removed from the surface of the restoration or appliance and opposing tooth or teeth after the removal of the restoration or appliance has been effectuated, with no adverse affect on the surface of the restoration or opposing tooth or teeth, leaving the surface of the restoration, the opposing tooth or teeth, and the restoration itself in the same condition as it was before the removal of the restoration was initiated.

3. The force used in the method of the invention in the removal of the firmly affixed, binding, stuck or cemented restorations or appliances is the muscular force of the jaws of the patient in an opening and closing direction, the jaws closing with sufficient pressure to compress the substance to approximately two-thirds of its bulk, and opening with a rapid and forceful jerking movement.

4. The restoration-removal substance aided by a mechanical device, or by a skeletal muscular force only, is the only means available for safely removing a firmly affixed, binding, stuck or locked-in coping post from an endodentically treated tooth, since any angular force applied could fracture the tooth's root.

The substance described above, which is used to remove firmly affixed, binding, stuck or cemented restorations and appliances in accordance with the teaching of the present invention, may be composed of any combination of materials, natural or artificial, vegetable, animal, mineral, or chemical elements which create a substance, which when placed in contact, and compress under sufficient pressure against the surface of the restoration or appliance to be removed, at a temperature range tolerable in the oral cavity, forms a strong temporary adhesive bond with the surface of the firmly affixed, binding, stuck or cemented restoration sufficient to cause its removal when sufficient specific directional muscular or other force is applied in the reverse direction to that in which the restoration was initially seated.

The malleable substance may be formed, for example, to have the property that when the compressive force is stopped, the substance attempts to return to its original shape and size creating its strong, temporary adhesive properties capable of, when reverse force is applied, removing all types of dental restorations that are binding, stuck, firmly affixed, locked in place or cemented. The substance may have the following composition:

| | |
|---|---|
| Sugar | 20 pounds |
| Glucose | 20 pounds |
| Water | 5 pounds |
| Natural gum | 44 pounds |
| Water | 4½ gallons |
| Gelatin | 3 pounds |

| -continued | |
|---|---|
| Glycerin | Trace |

Any one or more of the aforesaid elements may be eliminated, or others may be added, to create the desired malleable substance or compound with sufficient adhesive properties to achieve the desired results. The substance can be formed into any shape or size desired. The substance shape does not provide for any means of mechanical grasping or attachment to a tool. The substance adhesive properties are created by the substance formulation and its properties developed under compression.

The process of the invention may be used for the removal of all types of restorations and appliances that are firmly affixed, binding, or stuck at the time of fitting to determine whether marginal fit and occlusion are correct. The aforesaid substance permits the withdrawal of the firmly affixed, binding, or stuck restoration in the exact reverse direction to that in which the restoration was originally placed on or in the tooth, thereby reducing marginal distortion of the restoration to a minimum, and preventing fracture of the restoration when it is formed of porcelain or acrylic. Also, the substance permits the removal of temporary crowns and bridges, cemented to the tooth or teeth while the permanent crowns or bridges are being fabricated, enables salvage of the temporary crown or bridge so that it can be re-used and re-cemented while the laboratory work is being completed. Such withdrawals or removals are accomplished without the use of ancillary fixtures or tools, and only by the jaw actions of the patient and the force created thereby.

Removal of the firmly affixed, binding, stuck or cemented restorations or appliances can be accomplished by the process of the invention with minimal chance of tooth fracture. The process, moreover, enables the crown or bridge restoration to be salvaged and to be re-cemented when the problem causing its removal is corrected, so long as the recurrent decay or reason for removal of the cemented restoration has not destroyed the integrity of tooth preparation to re-receive the salvaged restoration. This is in contradistinction to the prior art methods and devices which distort or destroy the restoration.

BRIEF DESCRIPTION OF THE DRAWINGS

FIGS. 5A, 5B and 5C show the process of the invention used to remove a firmly affixed, binding, stuck or cemented bridge;

FIGS. 6A, 6B and 6C show the process of the invention, in a further embodiment, used to remove a firmly affixed, binding, stuck or cemented jacket from an upper anterior tooth;

FIG. 7 is a schematic representation showing the process of the invention, in a further embodiment, used to remove a firmly affixed, binding, stuck or cemented three-unit bridge;

FIGS. 8A, 8B and 8C are schematic representations of the process of the invention, in a further embodiment, used to remove a firmly affixed, binding, stuck or cemented crown from an upper posterior tooth;

FIG. 9 is a schematic representation of yet a further embodiment of the process of the invention; and FIG. 10 is a schematic representation of yet another embodiment of the invention.

DETAILED DESCRIPTION OF THE ILLUSTRATED EMBODIMENTS

Figure 1:
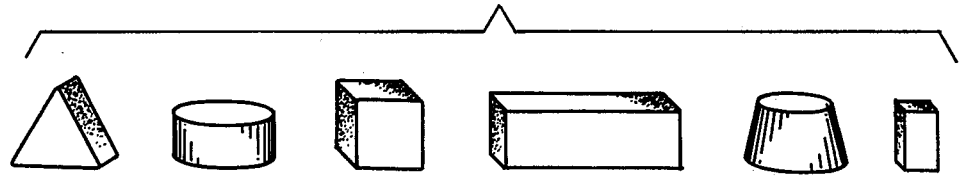
FIG. 1 is a perspective representation of the various shapes that the adhesive substance may take; with no provision in the shapes of the substance for attachment or clamping to or use of a tool or fixture.

The adhesive surface described above may be formed into various shapes with no provision of the shape for attachment to a tool, as shown in FIG. 1, to be used in removing all forms of firmly affixed, binding, stuck or cemented dental restorations. As described above, the adhesive substance may be used for the precementation removal of firmly affixed, binding, or stuck dental restorations and for the removal of previously cemented restorations. The process of the invention has a feature in that it serves to remove all restorations in a vertical direction without marginal distortion or destruction of the restoration, and no provision in the design of the shape of the substance is made for attachment of the substance to a tool or for mechanical grasping.

The primary purpose of a pre-cementation try-on of a dental restoration is to check the accuracy of its fit, and to finish the margin of the restoration with respect to the tooth prior to cementation. On many occasions at the time of fitting, the restoration snaps or locks into a proximal contact undercut, or the preparation's walls are excessively long and parallel, and in either event the restoration is binding and stuck tightly in place requiring substantial force be applied for its removal. There is a tendency for marginal distortion to occur to the restoration, when the firmly affixed, binding or stuck restoration is removed from the tooth to condition it for cementation, when presently available devices and methods are used. By the use of the process of the invention, the firmly affixed, binding, stuck or locked-on restoration can be removed without any marginal distortion or destruction to the restoration integrity because of the vertical direction of removal achieved by the process of the invention, corresponding to the direction for which the restorations are designed to go in place, be finished, and be cemented. No grasping with clamps or forceps is necessary or prying with instruments.

An even more important application of the use of the substance and the process of the invention is the removal of cemented dental restorations for whatever reason necessary. This feature of the invention will possibly create a whole new philosophy in restorative dentistry and the use of dental cements. Previous attempts in dentistry were to develop a permanent cement for cementation of fixed prostheses. The "permanent" cement has yet to be invented and the teachings of this invention now provides dentistry with a means of removing cemented fixed protheses for routine periodic check-ups to determine health of tissues and teeth supporting the protheses. This has not been possible in the past due to prior art.

As mentioned above, the process of the invention is extremely useful for the removal of cemented restorations, whenever such removal is required.

The process of the invention also eliminates the hazard of cracking and/or flaking of porcelain or acrylic restorations which results from their removal by other than vertical withdrawal, which causes marginal distortion of the inner metal which, in turn, tends to fracture the acrylic or porcelain of the restoration when prior art techniques are used. The process also may be used in the removal of firmly affixed, binding, stuck or cemented fixed bridgework without any tendency for marginal distortion of the abutment casings or fracture of the abutment teeth.

Figure 2A:
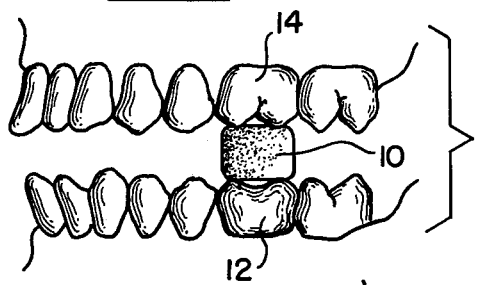
FIGS. 2A, 2B and 2C are schematic representations showing the manner in which the process of the invention may be practiced to remove, for example, a firmly affixed, binding, stuck or cemented crown from a lower posterior tooth, in which adhesion is provided by the adhesive substance only between the opposing tooth and the crown, with removal force being provided by forceful muscular opening of the mouth.
Figure 2B:
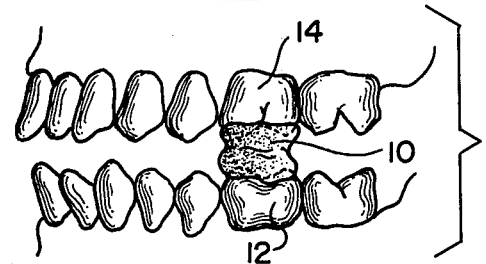
Figure 2C:
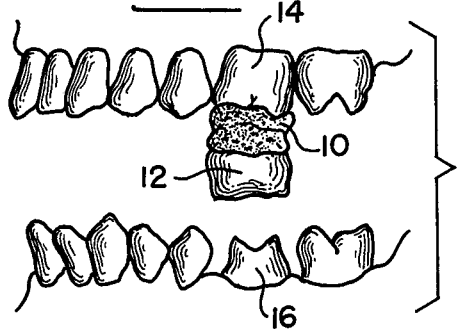

The process of the invention, for example, may be used for the removal of three-quarter, modified or full crowns, formed of gold, or other metal, or of porcelain or acrylic, which are firmly affixed, binding, stuck or cemented, such as shown in FIGS. 2A, 2B and 2C, not requiring the use of any mechanical means or tools to place or hold the substance.

Figure 3A:
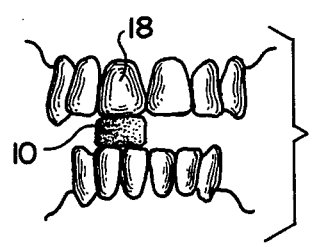
FIGS. 3A, 3B and 3C are schematic diagrams showing the practice of the process of the invention in the removal of a firmly affixed, binding, stuck or cemented jacket from an upper anterior tooth, in which adhesion exists only between the jacket and the lower anterior teeth, and the force of removal is the muscular force applied by the patient in a forceful opening of the mouth.

In the process represented by FIGS. 2A, 2B and 2C, a strongly adhesive substance 10, composed of appropriate ingredients such as described above, is placed on a firmly affixed, binding, stuck or cemented crown 12 on the lower tooth 16 which is to be removed. The patient then closes his jaws so that the substance 10 engages a corresponding upper tooth 14 (FIG. 3A). The patient then bites down on the substance (FIG. 2B) to compress the substance to at least 50% of its bulk and cause it firmly to adhere due to the substances adhesive properties developed under compressive force, against the crown 12 and his upper tooth 14. The patient then holds a non-compressing continual force against the substance 10 for 8-10 seconds, as the substance 10 attempts to return to its original form, thus creating the adhesion required between the substance and the crown 12 and tooth 14 to effect the removal of the crown 12. The patient then opens his jaws with a quick rapid forceful jerking motion causing the substance 10, which is now strongly but temporarily adhering to the crown 12 and tooth 14, to remove the crown from the tooth 16 in a vertical direction without marginal distortion.

Subsequently, the substance 10 may be removed from the tooth 14 after crown 12 has been removed and the adhesive force has lessened due to the substance 10 being no longer under compression force. The substance 10 may be removed from tooth 14 and crown 12 by any suitable solvent, without any adverse effect whatever to the tooth or to the crown.

It should be noted that for the adhesive substance 10 properly to perform its removal function, the patient must open his mouth with a quick rapid forceful jerking action. Slow opening of the mouth will not remove a firmly adhering, stuck, binding or cemented crown, due to the lessening of the adhesive characteristics of the substance 10.

Attachment of the substance to a tool is possible if sufficient compressive force is applied to cause its adhesion to the surface of the tool, but the force required for removal of firmly affixed, binding, stuck or cemented crowns cannot be achieved with finger pressure and would result in angular force not in the line of placement or drawn of the crown and similar to the prior art.

Figure 3B:
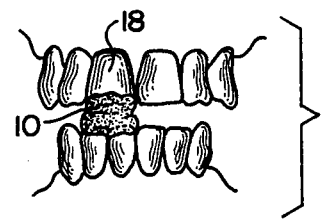
Figure 3C:
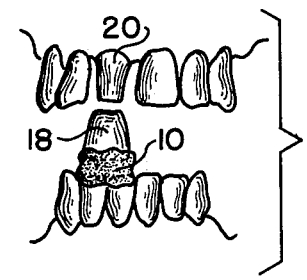

The process shown in FIGS. 2A, 2B and 2C is used for the removal, for example, of a firmly affixed, binding, stuck or cemented metal crown from a posterior tooth. In FIGS. 3A, 3B and 3C, the substance 10 is used to remove, for example, a porcelain jacket 18 from an anterior upper tooth 20, using the same steps as in FIGS. 2A, 2B and 2C.

Specifically, in the practice of the process shown in FIGS. 2A, 2B, 2C and 3A, 3B, 3C, the first step is to place the substance 10 on the restoration. The patient then slowly closes his tooth, or teeth, against the substance 10 until the substance is compressed to approximately 50-75% of its original bulk. The patient then holds his jaws at this point with constant, incompressible force for about one-half to three-quarters of a minute to allow time for the substance to develop its properties of strong adhesion sufficient to remove the firmly affixed, binding, stuck or cemented dental restoration. The patient then opens his jaws with a quick rapid forceful jerking opening motion. The substance will stick to the tooth 14 of the patient and to the restoration 12, thus removing the restoration from the tooth 16 in a vertical direction, eliminating crown distortion and minimizing patient and tooth trauma.

Care in selection of the opposing tooth is necessary in this process to determine its integrity. If doubt exists as to the integrity of the opposing tooth, then one of the flat surface embodiments should be used. The substance 10 adheres to the surface of the extraneous member and does not require mechanical clamping thereto. No provision is made in the design or the shape of the substance for attachment to any embodiment.

The process of the invention may also be used for the removal of firmly affixed, binding, stuck or cemented inlays by the same steps. However, in the removal of inlays, prior to placing the substance 10 on the restoration, the surface of the tooth which is not covered by the restoration is carefully coated with a separating medium, not allowing any of the medium to cover the surface of the restoration, such as green soap solution, petroleum jelly, and the like, to prevent the substance from sticking to the natural tooth. Then, when the patient opens his jaws in the manner described above, the substance will stick only to the inlay pulling the inlay free in a vertical direction in its line or draw.

Figure 4A:
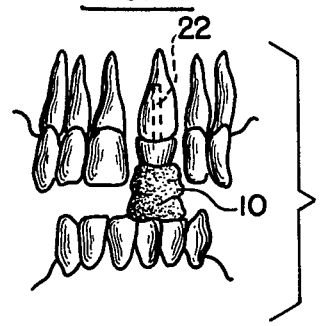
FIGS. 4A and 4B are schematic representations showing the process of the invention used to remove a firmly affixed, binding or stuck coping post from an endodontically treated tooth.

As shown in FIG. 4A, the process of the invention may also be used for the removing of a firmly affixed, stuck or binding coping post 22 from an endodentically treated tooth. The process is most important in this application, since any angular force applied to the coping post could fracture the root of the tooth and cause a total failure of the proposed restoration. In FIG. 4A, the coping post is removed by the patient opening his jaws in the manner described above.

Figure 4B:
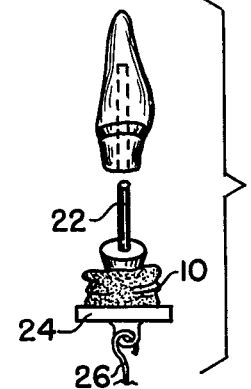

In FIG. 4B, the substance 10, instead of being attached to the teeth of the patient, is attached to a flat adhesion plate 24, and the coping is removed by applying an appropriate external force to the plate by way, for example, of a hook and reverse mallet 26 which exerts the sufficient forceful snapping precise vertical force on the coping to remove the post without any angular force being applied thereto. The hook and reverse mallet applies a percussion force similar to the rapid forceful snapping jerking opening movement of the jaws. As noted above, the strong temporary adhesive force of substance 10 will not be in effect if a steady pulling force is applied, such as the use of the fingers would create pulling on a tool.

In FIGS. 5A, 5B and 5C, the substance 10 is used for the removal of a firmly affixed, binding, stuck or cemented lower bridge, this being achieved by inserting the substance between the end teeth of the bridge and corresponding teeth of the patient, as shown in FIG. 5A, and by causing the patient to close his jaws to compress the substance, as shown in FIG. 5B, holding a constant non-compressing pressure for a predetermined time, and then by causing the patient to open his jaws with a quick forceful rapid jerking movement to remove the bridge, as shown in FIG. 5C. No tool is used to place the substance on the bridge or in the mouth and no provision of the design of the substance shape is made for mechanical clamping or grasping.

In FIGS. 6A, 6B and 6C, the substance 10 is used to remove a jacket 30, firmly affixed, binding, stuck or cemented, from an anterior tooth by an external force applied to the flat pressure plate 24 by a hook and external percussion-reverse mallet force 26. The flat plate has no means provided for grasping or clamping of the substance 10. The adhesion of the substance to the flat plate is achieved by the substance 10 adhesive properties developed under compressive force by jaw action of the patient.

In FIG. 7, the flat pressure plate 24, and external force applied thereto through hook and external force 26 is used to remove a firmly affixed, binding, stuck or cemented anterior three-unit bridge 32. No mechanical means is provided for attachment of the substance 10 to flat plate 24.

FIGS. 8A, 8B and 8C show the process of the invention applied to the removal of a firmly affixed, binding, stuck or cemented crown 36 from a posterior upper tooth 40, when the opposing lower tooth is weak or missing. In this case, a flat pressure plate 38 is used which cpans the missing or weak tooth, and the substance 10 is placed between the flat pressure plate 38 and crown 36, and between the flat pressure plate 38 and the lower teeth 42 and 44 adjacent to the missing tooth. When the patient closes his jaws, the substance is compressed and forcefully adheres to the flat surface of pressure plate 38, and to crown 36 and teeth 42 and 44. No mechanical means are provided for holding the substance on the pressure plate 38. The substance adheres to the flat surface of plate 38 by its adhesive properties developed under compression in the same manner it adheres to crown 36, and teeth 42 and 44.

In the embodiment of FIG. 9, the patient instead of opening his mouth, closes his mouth to remove the restoration. As illustrated, the lever-like member 50 is pivotally supported by a fulcrum 52 which, in turn, is supported by a pad 54 on the lower teeth of the patient. One end of member 50 is compressed against the substance 10 which also is compressed against a firmly affixed, binding, stuck or cemented crown 56 to be removed from a lower posterior tooth. The other end of member 50 is engaged by the upper teeth of a patient through a bite pad 58. A stop pad 60 is also mounted on the last-named end of the member 50 and above the fulcrum. When the patient closes his mouth in a quick forceful jerking manner, the member 50 is turned in a counterclockwise direction to remove the firmly affixed, binding, stuck or cemented crown from the tooth. No mechanical means are provided for holding the substance on the embodiment.

The embodiment of FIG. 10 exerts a somewhat similar action on crown 56 through the substance 10. In the latter embodiment the member 50 is pivotally supported between a double fulcrum 62, and an external force is applied to the left-hand end of the member 50 through a hook and external force 64, which may be a reverse mallet, or the like. No mechanical means is provided for holding substance 10 on member 50 or design of the shape of the substance 10 for being held by any means or tool.

When the external rapid, reverse hammering force is applied, and the patient holds his mouth closed against the fulcrum plate 62, the combined action causes the substance 10 to pull the firmly affixed, binding, stuck or cemented crown off the tooth.

The invention provides, therefore, an improved process and means for removing firmly affixed, binding, or stuck dental restorations during their pre-cementation stage, or after cementation, without distorting in any way the restoration, and without destroying or otherwise affecting the integrity of the restoration, and with minimal trauma to the periodontal tissues, tooth or patient.

The shape of the substance does not provide for any means of mechanical clamping, grasping or attachment to a tool or embodiment. The adhesive force of the substance developed under compression achieved by the patient's jaw action is the force for compression and subsequent removal of firmly affixed, stuck or binding dental restorations when the patient opens his mouth as described.

Although various embodiments of the process and means of the invention have been shown and described, modifications may be made. It is intended in the claims to cover the modifications which come within the spirit and scope of the invention.

What is claimed is:

1. A process for the removal of a firmly affixed, stuck, binding or cemented dental restoration, and the like, from a tooth of a patient, which comprises: inserting an adhesive substance between the surface of the restoration and at least one opposing tooth of the patient; causing the patient to close his jaws to compress the adhesive substance against the surface of the restoration with at least 25 pounds pressure until a firm adhesive bond is achieved; and causing the patient to open his jaws in a snapping quick forceful rapid jerking movement to apply a reverse force to the adhesive substance in a direction to effect a removal of the restoration from the tooth.

2. The process defined in claim 1, and which also includes the step of causing the patient to hold a constant noncompressing force on the substance for a predetermined time interval after the substance has been compressed to cause the substance to exhibit temporary strong adhesive properties sufficient to remove the firmly affixed, binding or cemented dental restorations.

3. The process defined in claim 1, in which said firmly affixed, binding, stuck or cemented restoration comprises a coping post inserted into an endodentically treated tooth.

4. The process defined in claim 1, in which said firmly affixed, binding, stuck or cemented restoration comprises a multi-tooth bridge, and in which two separate units of the substance are respectively compressed against the teeth at each end of the bridge and the opposing teeth.

5. The process defined in claim 4, and which comprises causing the patient to close his jaws to compress the two units of the adhesive substance and to cause the two units of the adhesive substance to form respective additional adhesive bond with two teeth of the patient in the arch opposite to the bridge; causing the patient to hold a constant, non-compressing force against the two units of the substance for a predetermined time interval to cause the substance to exert adhesive properties; and causing the patient to open his jaws in a quick forceful jerking motion to cause the two units of the substance to pull the firmly affixed, binding, stuck or cemented bridge away from the abutment teeth.

6. The process defined in claim 1, and which includes the step of compressing a flat plate against the side of the adhesive substance opposite to the restoration to form an adhesive bond between the plate and the adhesive substance; and applying said force to said plate.

7. The process defined in claim 6, and which includes the step of placing at least one separate unit of said adhesive substance on the opposite side of said flat plate, causing the patient to close his jaws to compress the first-named and second units of the adhesive substance and to cause the second unit of the adhesive substance to form a second adhesive bond with a tooth of the patient in the arch opposite to the firmly affixed, binding, stuck or cemented restoration; causing the patient to hold a noncompressing force against the substance for a predetermined interval; and causing the patient to open his jaws in a rapid forceful jerking motion to pull the firmly affixed, binding, stuck or cemented restoration from the first-named tooth.

8. The process defined in claim 1, and which includes compressing one end of a flat plate against the side of the adhesive substance opposite to the firmly affixed, binding, stuck or cemented restoration to form an adhesive bond between the surface of the flat plate and the adhesive substance; introducing a fulcrum between an intermediate point on the plate and the teeth of the patient, and exerting said force on the other end of the flat plate.

9. The process defined in claim 8, and which comprises causing the patient to close his jaws in a rapid forceful jerking quick movement to apply said force.

* * * * *